United States Patent
Maywald et al.

(10) Patent No.: US 8,207,354 B2
(45) Date of Patent: Jun. 26, 2012

(54) PROCESS FOR PREPARING ALKYL 2-ALKOXYMETHYLENE-4,4-DIFLUORO-3-OXOBUTYRATES

(75) Inventors: Volker Maywald, Ludwigshafen (DE);
Sebastian Peer Smidt, Oftersheim (DE);
Bernd Wolf, Fussgoenheim (DE);
Christopher Koradin, Ludwigshafen (DE); Thomas Zierke, Boehl-Iggelheim (DE); Michael Rack, Eppelheim (DE);
Michael Keil, Freinsheim (DE)

(73) Assignee: BASF SE, Ludwigshafen (DE)

( * ) Notice: Subject to any disclaimer, the term of this patent is extended or adjusted under 35 U.S.C. 154(b) by 19 days.

(21) Appl. No.: 12/919,842

(22) PCT Filed: Feb. 27, 2009

(86) PCT No.: PCT/EP2009/052378
§ 371 (c)(1),
(2), (4) Date: Aug. 27, 2010

(87) PCT Pub. No.: WO2009/106619
PCT Pub. Date: Sep. 3, 2009

(65) Prior Publication Data
US 2011/0004002 A1    Jan. 6, 2011

(30) Foreign Application Priority Data
Feb. 29, 2008 (EP) .................... 08102197

(51) Int. Cl.
C07D 231/10 (2006.01)
C07C 69/00 (2006.01)
(52) U.S. Cl. ..................... 548/374.1; 560/174
(58) Field of Classification Search ............... 548/374.1; 560/174
See application file for complete search history.

(56) References Cited

U.S. PATENT DOCUMENTS

| | | | |
|---|---|---|---|
| 5,618,951 | A | 4/1997 | Britton |
| 7,994,207 | B2 | 8/2011 | Zierke et al. |
| 2006/0276656 | A1 | 12/2006 | Lantzsch et al. |
| 2008/0015244 | A1 | 1/2008 | Dunkel et al. |
| 2008/0108686 | A1 | 5/2008 | Gewehr et al. |
| 2010/0022782 | A1 | 1/2010 | Zierke et al. |
| 2010/0069646 | A1 | 3/2010 | Sukopp et al. |

FOREIGN PATENT DOCUMENTS

| | | |
|---|---|---|
| EP | 1 854 788 | 11/2007 |
| EP | 1 997 808 | 12/2008 |
| WO | WO 92/12970 | 8/1992 |
| WO | WO 93/11117 | 6/1993 |
| WO | WO 03/070705 | 8/2003 |
| WO | WO 2005/044804 | 5/2005 |
| WO | WO 2005/123690 | 12/2005 |
| WO | WO 2007/031323 | 3/2007 |
| WO | WO 2007/115766 | 10/2007 |
| WO | WO 2008/053043 | 5/2008 |

OTHER PUBLICATIONS

Desirant, T., Sur le difluoracetyl-acetate d'ethyle//Ethyl difluoroacetoacetate:, Bulletin de la classe des classe—Academie Royale de Belgique, 15, (1929), 966-982, XP009097294.
Jagodzinska, S. et al., "Studies on a three-step preparation of β-fluoroalkyl acrylates from fluoroacetic esters", Tetrahedron, 63, (2007) 2042-2046.
Natta, G., et al., "The Distribution of Products in a Series of Consecutive Competitive Reactions", Contribution from The Instituto di Chimica Industriale Poliechnico of Milano, 74, (1951), 3152-3156.
International Search Report for International Application No. PCT/EP2009/052378, Apr. 24, 2009.
International Preliminary Report on Patentability for International Application No. PCT/EP2009/052378, Sep. 10, 2010.

*Primary Examiner* — Rebecca Anderson
*Assistant Examiner* — Samantha Shterengarts
(74) *Attorney, Agent, or Firm* — Brinks Hofer Gilson & Lione

(57) ABSTRACT

A process for preparing alkyl 2-alkoxymethylene-4,4-difluoro-3-oxobutyrates (VI)

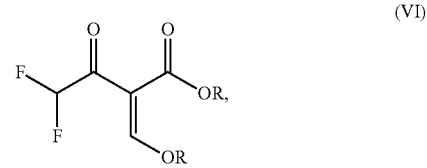

where R is methyl or ethyl,
from crude reaction mixtures of alkyl 4,4-difluoroacetoacetates (I)

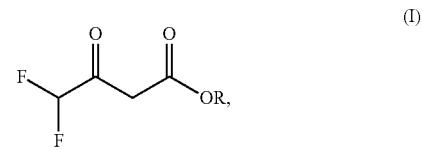

by
a) reacting

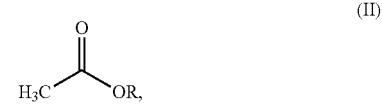

alkyl acetate

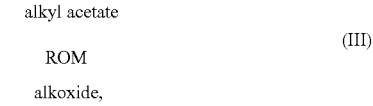

alkoxide, where M is a sodium or potassium ion, and

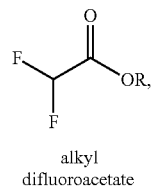

(IV)

alkyl difluoroacetate without additional solvent to form an enolate (V)

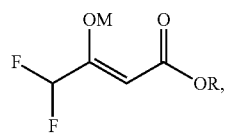

(V)

b) releasing the corresponding alkyl 4,4-difluoroacetoacetate (I) from the enolate (V) by means of acid, c) removing the salt formed from cation M and acid anion as a solid and d) converting (I), without isolation from the crude reaction mixture, to the alkyl 2-alkoxymethylene-4,4-difluoro-3-oxobutyrate (VI), and the use of (VI) for preparing 1-methyl-3-difluoromethyl-pyrazol-3-ylcarboxyates VII

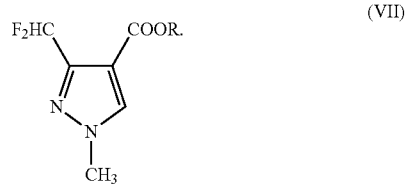

(VII)

19 Claims, No Drawings

PROCESS FOR PREPARING ALKYL 2-ALKOXYMETHYLENE-4,4-DIFLUORO-3-OXOBUTYRATES

This application is a National Stage application of International Application No. PCT/EP2009/052378 filed Feb.27, 2009, the entire contents of which is hereby incorporated herein by reference. This application also claims the benefit under 35 U.S.C. §119 of European Patent Application No. 08102197.4, filed Feb. 29, 2008, the entire contents of which is hereby incorporated herein by reference.

The present invention relates to a process for preparing alkyl 2-alkoxymethylene-4,4-difluoro-3-oxobutyrates of the formula (VI)

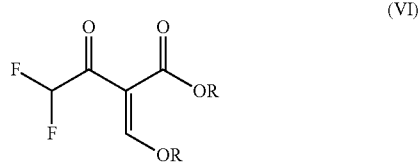
(VI)

where R is methyl or ethyl,
from crude reaction mixtures of alkyl 4,4-difluoroacetoacetates of the formula (I)

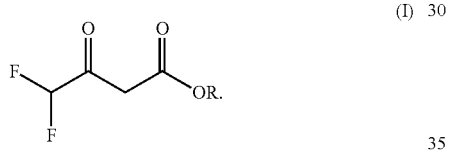
(I)

With respect to the preparation of I with R being ethyl, Y. Desirant, Bulletin de la SocietéChim. Belg. 39 (1930) discloses the reaction of a suspension of sodium ethoxide in dry ether first with ethyl difluoroacetate and then with ethyl acetate, and the release of ethyl 4,4-difluoroacetoacetate from the enolate formed by means of 10% aqueous sulfuric acid. For this process, in the best case, a yield of 65% is reported.

However, this process is not very suitable for an industrial scale preparation of the alkyl 2-alkoxymethylene-4,4-difluoro-3-oxobutyrates (VI) since the yields for the preparation of the alkyl 4,4-difluoroacetoacetates (I) are unsatisfactory (due to some product being lost during purification by destillation) and the reaction times of 5 days are unacceptably long. Moreover, the handling of the ether used as the solvent would be disadvantageous, since its very low boiling point would necessitate complicated measures for preventing evaporation losses. Moreover, this solvent tends to form peroxides, for which reason special safety measures have to be taken.

Other processes for preparing alkyl 4,4-difluoroacetoacetates described in the literature have the disadvantage that bases which are expensive and/or difficult to use industrially, such as sodium hydride or lithium diisopropylamide, are used (cf. McBee et al., J. Am. Chem. Soc., 75, 3152-3153 (1952) and S. Jagodzinska et al., Tetrahedron 63, 2042-2046 (2007)), or the reaction is carried out in an additional solvent to be handled (WO 2007/115766, Example H1).

A process for the preparation of ethyl 2-ethoxymethylene-4,4-difluoro-3-oxobutyrate is disclosed in WO 2005/123690 (page 21, paragraph 2.)). However, the precursor compound ethyl 4,4-difluoroacetoacetate is obtained according to another method and purified by distillation before the further conversion. These high temperatures, however, adversely affect the yield of the ethyl 2-ethoxymethylene-4,4-difluoro-3-oxobutyrate.

It was accordingly an object of the invention to provide an industrially simple process for preparing the alkyl 2-alkoxymethylene-4,4-difluoro-3-oxobutyrates (VI).

Accordingly, it has been found that the alkyl 2-alkoxymethylene-4,4-difluoro-3-oxobutyrates (VI) are obtainable in high yields by
a) initially charging two of the following components (II), (III) and (IV)

alkyl acetate
(II)

ROM
alkoxide,
(III)

where M is a lithium, sodium or potassium ion, and

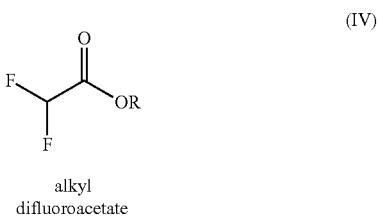
alkyl difluoroacetate
(IV)

and reacting this mixture with the third component without additional solvent to form an enolate of the formula (V)

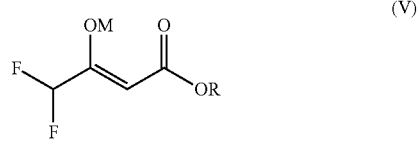
(V)

b) releasing the corresponding alkyl 4,4-difluoroacetoacetate of the formula (I)

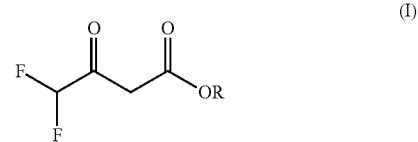
(I)

from the enolate of (V) by means of acid,
c) removing the salt formed from cation M and the acid anion as a solid and
d) converting (I), without isolation from the crude reaction mixture, to the alkyl 2-alkoxymethylene-4,4-difluoro-3-oxobutyrate of the formula (VI).

The starting compounds (II), (III) and (IV) are commercially available or can be prepared in a manner known per se.

Preferably, the alkyl acetate (II) and alkyl difluoroacetate (IV) are initially charged and the alkoxide (III) is metered in.

The amount of alkyl acetate (II) is such that the reaction mixture with alkoxide (III) and alkyl difluoroacetate (IV) either gives rise to a readily stirrable suspension or becomes homogeneous. Advantageously, the molar ratio of alkyl acetate (II) to alkoxide (III) is from 0.8:1 to 10:1, especially from 2:1 to 4:1, most preferably from 2.3:1 to 3:1.

The molar ratio of alkyl difluoroacetate (IV) to alkyl acetate (II) is preferably from 1:0.8 to 1:20, especially from 1:2 to 1:3.

The metered addition of (II), (III) and (IV) typically proceeds over the course of from 0.1 to 20 hours, especially from 0.5 to 5 hours, more preferably from 0.5 to 3 hours.

The reaction temperature for the reaction stage a) is generally from −20° C. up to the boiling point of the reaction mixture, especially from 0 to 70° C.

The reaction can be carried out under standard pressure or under slightly elevated or reduced pressure. Typically, standard pressure is employed.

The alkyl 4,4-difluoroacetoacetate (I) is released from the enolate (V) in the presence of an acid such as hydrogen chloride, hydrogen bromide, hydrogen iodide, sulfuric acid, formic acid, acetic acid, oxalic acid, citric acid, methanesulfonic acid, or p-toluenesulfonic acid, preference being given to hydrogen chloride, in particular gaseous hydrogen chloride.

According to the present invention, the release of the alkyl 4,4-difluoroacetoacetate (I) from the enolate (V) is undertaken with an anhydrous acid or an acid with only a small water content.

A small water content is understood to mean from about 0.5 g to 5 g of water per mole of alkyl difluoroacetate (IV) used.

In this procedure, it may be advantageous to remove the inorganic salt formed from cation M and the acid anion in the course of the neutralization before the further processing of (I), for example, by means of filtration methods. With regard to the filtration of the salt, a particularly advantageous procedure is that in the presence of a small water content (for example when the HCl gas is introduced or when an acid with a small water content is used, such as conc. sulfuric acid). This generally gave rise to significantly shorter filtration times, which may be highly advantageous for the procedure on the industrial scale.

However, larger amounts of water should be avoided, unless the subsequent removal of an aqueous phase is intended, since the water would be troublesome in the conversion of (I) to (VI) or would lead to an increased consumption of feedstocks (orthoester and anhydride).

The amount of acid itself is not particularly critical. In general, from 0.7 to 5 mol of acid are used per mole of alkoxide (III) used, preferably from 0.8 to 2 mol of acid per mole of (III), more preferably from 0.9 to 1.3 mol of acid per mole of (III).

The release of (I) from (V) by means of acid (stage b)) is effected generally at from −10 to 50° C., especially from 5 to 30° C., and at standard pressure or slightly elevated pressure, up to about 3 bar.

According to the process of the present invention, the alkyl 4,4-difluoroacetoacetate (I), in the alkyl acetate (II) after removal of the inorganic salt and without purification, is reacted directly with orthoester $HC(OR)_3$ and acetic anhydride to give the alkyl 2-alkoxymethylene-4,4-difluoro-3-oxobutyrate (VI)

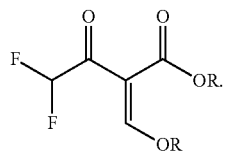

The conversion of (I) to the alkyl 2-alkoxymethylene-4,4-difluoro-3-oxobutyrate (VI) is effected normally at from 25 to 150° C. and at standard pressure or a slightly elevated pressure up to about 3 bar, especially at from 90 to 115° C. and standard pressure.

The molar ratio of orthoester to alkyl 4,4-difluoroacetoacetate (I) is preferably from 1:1 to 3:1, especially from 1.5:1 to 1.9:1.

When calculating the amount of acetic anhydride required for a complete conversion, the alcohol formed from the alkoxide (III) additionally has to be considered.

Typically, the amount of acetic anhydride is from 2 to 8 mol per mole of alkyl 4,4-difluoroacetoacetate (I).

The process products (VI) are valuable intermediates for preparing 1-methyl-3-difluoromethylpyrazol-4-ylcarboxylates (VII)

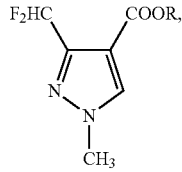

which are obtainable, for example, by cyclizing (VI) with methylhydrazine (see U.S. Pat. No. 5,093,347, EXAMPLE 1). 1-Methyl-3-difluoromethylpyrazol-4-ylcarboxylates in turn are important starting materials for preparing fungicidally active pyrazol-4-ylcarboxamides.

WORKING EXAMPLES

Example 1 a) Ethyl 4,4-difluoroacetoacetate (Release from the Enolate with Gaseous Hydrogen Chloride in the Presence of a Small Amount of Water)

733.1 g (8.32 mol) of ethyl acetate and 397.6 g (3.2 mol) of ethyl difluoroacetate (99.9%) were initially charged at 25° C. and 238.7 g (3.437 mol) of sodium ethoxide (98%) were metered form 25 to 65° C. with stirring in the course of 1.3 hours.

Thereafter, the reaction mixture was stirred at 65° C. for a further 2 hours and then cooled to 25° C.

To the resulting solution, 8 g (0.444 mol) water were added. Then, at 25 to 31° C., 160.5 g (4.40 mol) of HCl gas were introduced within 2 hours, which formed a suspension (precipitation of sodium chloride). Subseqently, a small amount (133.2 g) of low boilers (133.2 g; ethanol, ethyl acetate; excess HCl) were removed by destillation (internal temperature: 25-34° C.; pressure: 150 mbar). The precipitated sodium chloride was filtered off and the solid was washed four times with 360 g of ethyl acetate.

The resulting filtrate (2171 g) comprised 22.6% by weight of the desired product of value (GC analysis, quantification with internal standard).

The yield, based on ethyl difluoroacetate used, was 92.4%.

b) Conversion of ethyl 4,4-difluoroacetoacetate to ethyl 2-ethoxymethylene-4,4-difluoro-3-oxobutyrate 2274.9 g of acetic anhydride (22.08 mol) were initially charged in a stirred vessel and heated to 110° C. Within 2 hours, 2171 g of the ethyl 4,4-difluoroacetoacetate solution from synthesis example 1a) (22.6% solution in ethanol/ethyl acetate) and 822.7 g (5.44 mol) of triethyl orthoformate (98%) were metered in in parallel. After about half had been fed in, reflux set in. At the end of the metered addition, the internal temperature was 95° C. The mixture was stirred at reflux temperature for a further 7 hours and then cooled to 25° C. At a pressure of 150 mbar, the low boilers (ethyl acetate, acetic acid, acetic anhydride, triethyl orthoformate) were distilled off at internal temperature 40-90° C. To complete the removal, the pressure was lowered to 5 mbar at 90° C., and the distillation bottoms were subsequently stirred at 95° C./5 mbar for 0.5 hours. The obtained distillation residue (658.8 g) comprised 95.5% by weight of the desired ethyl 2-ethoxymethylene-4,4-difluoro-3-oxobutyrate. This corresponds to an overall yield over the two synthesis stages of 88.5% based on the ethyl difluoroacetate used in working example 1a).

Example 2

Ethyl 4,4-difluoroacetoacetate (Release from the Enolate with Gaseous Hydrogen Chloride)

141.2 g (1.6 mol) of ethyl acetate were initially charged at 25° C. and 45.9 g (0.66 mol) of sodium ethoxide (98%) were added with stirring. After the suspension had been cooled to 5° C., 76.7 g (0.6 mol) of ethyl difluoroacetate (97%) were metered in at internal temperature from 5 to 13° C. within 2.83 hours. Thereafter, the reaction mixture was heated to 65° C., stirred at this temperature for a further 2 h and then cooled to 20° C. (264.3 g of solution).

At 21 to 31° C., 26.5 g (0.726 mol) of HCl gas were introduced within 30 minutes, which formed a suspension (precipitation of sodium chloride). 51.2 g of ethyl acetate were added to the suspension and then 21.2 g of low boilers were distilled off at internal temperature 31° C. and a pressure of 150 mbar (removal of excess hydrogen chloride). After 5 g of kieselguhr (filtration aid) had been added, the precipitated sodium chloride was filtered off and the solid was washed with ethyl acetate. The resulting filtrate (438 g) comprised 20.9% by weight of the desired product of value (GC analysis, quantification with internal standard).

The yield (based on ethyl difluoroacetate used) was 91.9%.

Example 3

Ethyl 2-ethoxymethylene-4,4-difluoro-3-oxobutyrate 427.8 g of acetic anhydride (4.15 mol) were initially charged in a stirred vessel and heated to 110° C. Within 2 hours, 438 g of crude ethyl 4,4-difluoroacetoacetate from synthesis example 2 (20.9% solution in ethanol/ethyl acetate) and 145.3 g (0.96 mol) of triethyl orthoformate were metered in in parallel. After about half had been fed in, reflux set in at 106° C. At the end of the metered addition, the internal temperature was 94° C. The mixture was stirred at reflux temperature for a further 6 hours and then cooled to 25° C. At a pressure of 150 mbar, the low boilers (ethyl acetate, acetic acid, acetic anhydride, triethyl orthoformate) were distilled off at internal temperature 40-90° C. To complete the removal, the pressure was lowered to 10 mbar at 90° C., and the distillation bottoms were subsequently stirred at 95° C./10 mbar for 1 hour. The distillation residue (125.7 g) comprised 89.7% by weight of the desired ethyl 2-ethoxymethylene-4,4-difluro-3-oxobutyrate. This corresponds to an overall yield over the two synthesis stages of 84.6% based on the ethyl difluoroacetate used in working example 2.

Example 4

Ethyl 4,4-difluoroacetoacetate (Release from the Enolate with Methanesulfonic Acid)

47.06 g (0.533 mol) of ethyl acetate were initially charged at 25° C. and 15.3 g (0.22 mol) of sodium ethoxide (98%) were added with stirring. After the suspension had been cooled to 5° C., 25.6 g (0.2 mol) of ethyl difluoroacetate (97%) were metered in at internal temperature from 5 to 13° C. within 2.83 hours. Thereafter, the reaction mixture was heated to 65° C., stirred at this temperature for a further 2 hours and then cooled to 20° C. (88.1 g of solution).

At from 20 to 30° C., 21.2 g (0.22 mol) of methanesulfonic acid were added drop wise within 40 minutes, which formed a thick suspension (precipitation of sodium methylsulfonate). To dilute the suspension, 60 ml of ethyl acetate were added. The solid was filtered off and washed twice with ethyl acetate. The filtrate (209.2 g) comprised 13.9% by weight of the desired product of value (GC analysis: quantification with internal standard). The yield (based on ethyl difluoroacetate used) was 87.6%.

Example 5

Ethyl 4,4-difluoroacetoacetate (Release from the Enolate with Sulfuric Acid (98%))

45.9 g (0.53 mol) of ethyl acetate were initially charged at 25° C. and 14.96 g (0.22 mol) of sodium ethoxide (98%) were added with stirring. After the suspension had been cooled to 5° C., 24.9 g (0.2 mol) of ethyl difluoroacetate (99.88%) were metered in at internal temperature from 10 to 25° C. within 2.0 hours. Thereafter, the reaction mixture was heated to 65° C., stirred at this temperature for a further 2 hours and then cooled to 20° C.

20.4 g (0.2 mol) of sulfuric acid (98%, comprises 2% water) were metered into the solution (85.6 g) at from 20 to 25° C. within 20 minutes, which formed a thick suspension (precipitation of sodium hydrogensulfate). The precipitated salt was also filtered off and the solid was washed with ethyl acetate. The filtrate (166.1 g) comprised 19.1% by weight of the desired product of value (GC analysis, quantification with internal standard). The yield (based on ethyl difluoroacetate used) was 95.6%.

Example 6

Ethyl 4,4-difluoroacetoacetate (Release from the Enolate with Formic Acid)

47.06 g (0.533 mol) of ethyl acetate were initially charged at 25° C. and 15.3 g (0.22 mol) of sodium ethoxide (98%) were added with stirring. After the suspension had been cooled to 5° C., 25.6 g (0.2 mol) of ethyl difluoroacetate (97%) were metered in at internal temperature from 5 to 13° C. within 2.83 hours. Thereafter, the reaction mixture was heated to 65° C., stirred at this temperature for a further 2 h and then cooled to 20° C. (88.1 g of solution).

At 20° C., 10.3 g (0.22 mol) of formic acid were added drop wise within 40 minutes which formed a suspension (precipitation of sodium formate). The mixture was stirred at 25° C. for a further hour. The precipitated solid was filtered off and washed with ethyl acetate. The resulting filtrate (160.6 g) comprised 18% by weight of the desired product of value (GC analysis, quantification with internal standard). The yield (based on ethyl difluoroacetate used) was 87.1%.

Example 7

Ethyl 4,4-difluoroacetoacetate (Release from the Enolate with Gaseous Hydrogen Chloride in the Presence of a Small Amount of Water)

137.8 g (1.56 mol) of ethyl acetate were initially charged at 25° C. and 44.9 g (0.65 mol) of sodium ethoxide (98%) were added with stirring. After the suspension had been cooled to 5° C., 74.8 g (0.6 mol) of ethyl difluoroacetate (99.88%) were metered in at internal temperature from 10 to 25° C. within 2.0 hours. Thereafter, the reaction mixture was heated to 65° C., stirred at this temperature for a further 2 hours and then cooled to 20° C. (256.8 g of solution).

0.3 g of water was added to the solution (256.8 g) and then 27.7 g (0.759 mol) of HCl gas were introduced at from 21 to 31° C. within 30 minutes, which formed a suspension (precipitation of sodium chloride). 22.1 g of ethyl acetate were added to the suspension and then 14.2 g of low boilers (removal of excess HCl) were distilled off at internal temperature 33° C. and a pressure of 150 mbar. The precipitated sodium chloride was filtered off and the solid was washed with ethyl acetate. The resulting filtrate (356.3 g) comprised 26.6% by weight of the desired product of value (GC analysis, quantification with internal standard).

The yield (based on ethyl difluoroacetate used) was 94.6%.

Example 8

Ethyl 2-ethoxymethylene-4,4-difluoro-3-oxobutyrate 365.2 g of acetic anhydride (3.54 mol) were initially charged in the stirred vessel and heated to 110° C. Within 2 hours, 356.3 g of crude ethyl 4,4-difluoroacetoacetate from synthesis example 7 (26.5% ethyl 4,4-difluoroacetoacetate solution in ethanol/ethyl acetate) and 154.4 g (1.02 mol) of triethyl orthoformate were metered in in parallel. After about half had been fed in, reflux set in at 106° C. At the end of the metered addition, the internal temperature was 92° C. The mixture was stirred for a further 5 hours at reflux temperature and then cooled to 25° C. At a pressure of 150 mbar, the low boilers (ethyl acetate, acetic acid, acetic anhydride, triethyl orthoformate) were distilled off at internal temperature from 40-90° C. To complete the removal, the pressure is lowered to 5 mbar at 90° C., and the distillation bottoms are then stirred at 95° C./5 mbar for 1 hour. The resulting distillation residue (127.5 g) comprised 90.7% by weight of the desired ethyl 2-ethoxymethylene-4,4-difluoro-3-oxobutyrate. This corresponds to an overall yield over the two synthesis stages of 86.6% (based on the ethyl difluoroacetate used in working example 7).

The invention claimed is:

1. A process for preparing an alkyl 2-alkoxymethylene-4,4-difluoro-3-oxobutyrate of the formula (VI)

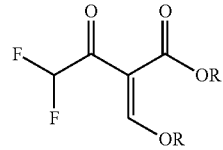

where R is methyl or ethyl, from crude reaction mixtures of alkyl 4,4-difluoroacetoacetate (I)

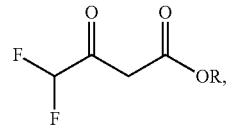

which comprises
a) initially charging two of the following components (II), (III) and (IV)

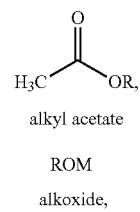

alkyl acetate

ROM (III)

alkoxide, where M is a lithium, sodium or potassium ion, and

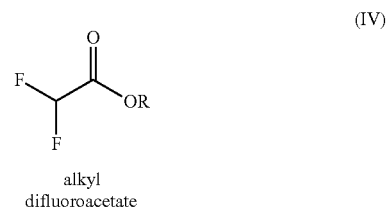

alkyl difluoroacetate and reacting this mixture with the third component to form an enolate of the formula (V)

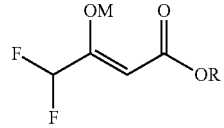

b) adding an acid to the reaction mixture to release the corresponding alkyl 4,4-difluoroacetoacetate of formula (I) from the enolate (V),
c) removing the salt formed from cation M and the acid anion as a solid and d) converting (I), without isolation from the crude reaction mixture, to the alkyl 2-alkoxymethylene-4,4-difluoro-3-oxobutyrate of the formula (VI).

2. The process according to claim 1, wherein process stage a) is carried out by initially charging alkyl acetate (II) and alkyl difluoroacetate (IV) and metering in the alkoxide (III).

3. The process according to claim 1, wherein (I) is released from (V) with exclusion of water or in the presence of a small water content.

4. The process according to claim 1, wherein the acid used for the release of (I) from (V) in process stage b) is hydrogen chloride, hydrogen bromide, hydrogen iodide, sulfuric acid, formic acid, acetic acid, oxalic acid, citric acid, methanesulfonic acid, or p-toluenesulfonic acid.

5. The process according to claim 1, wherein the release of (I) from (V) in process stage b) is carried out in the presence of a small water content.

6. The process according to claim 1, wherein the molar ratio of alkyl acetate (II) to alkoxide (III) is from 0.8:1 to 10:1.

7. The process according to claim 1, wherein the molar ratio of alkyl difluoroacetate (IV) to alkyl acetate (II) is from 1:0.8 to 1:20.

8. The process according to claim 1, wherein the molar ratio of alkoxide (III) to acid is from 1:0.7 to 1:5.

9. The process according to claim 1, wherein the reaction temperature for the reaction of (II), (III) and (IV) is from −20° C. up to 70° C.

10. A method of preparing a 1-methyl-3-difluoromethyl-pyrazol-3-ylcarboxylate of the formula VII

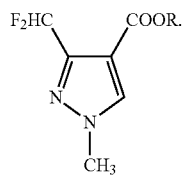

comprising preparing an alkyl 2-alkosymethylene-4,4- difluoro-3-oxobutyrate of the formula (VI)

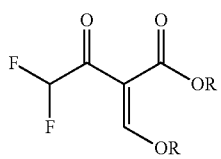

where R is methyl or ethyl, from crude reaction mixtures of alkyl 4,4 difluoroacetoacetate (I)

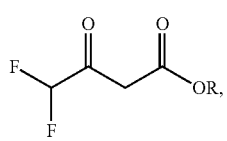

which comprises
a) initially charging two of the following components (II), (III) and (IV)

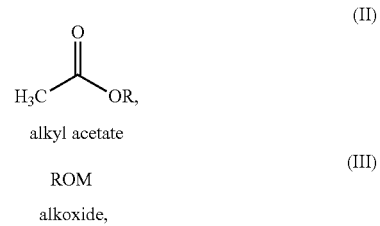

where M is a lithium, sodium or potassium ion, and

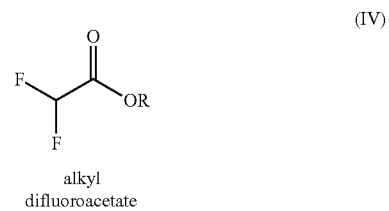

and reacting this mixture with the third component to form an enolate of the formula (V)

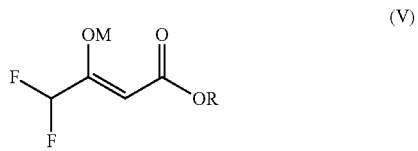

b) adding an acid to the reaction mixture to release the corresponding alkyl 4,4-difluoroacetate of formula (I) from the enolate(V),
c) removing the salt formed from cation M and the acid anion as a solid
d) converting (I), without isolation from the crude reaction mixture to the alkyl 2-alkoxymethylene-4,4-difluoro-3-oxobutyrate of the formula (VI)
e) cyclizing the compound of formula VI.

11. The method of claim 10, wherein said cyclizing comprises reacting the compound of formula VI with methylhydrazine.

12. The method according to claim 11, wherein process stage a) is carried out by initially charging alkyl acetate (II) and alkyl difluoroacetate (IV) and metering in the alkoxide (III).

13. The method according to claim 11, wherein, in the process of preparing the compound of formula (VI), (I) is released from (V) with exclusion of water or in the presence of a small water content.

14. The method according to claim 11, wherein, in the process of preparing the compound of formula (VI), the acid used for the release of (I) from (V) in process stage b) is hydrogen chloride, hydrogen bromide, hydrogen iodide, sulfuric acid, formic acid, acetic acid, oxalic acid, citric acid, methanesulfonic acid, or p-toluenesulfonic acid.

15. The method according to claim 11, wherein, in the process of preparing the compound of formula (VI), the release of (I) from (V) in process stage b) is carried out in the presence of a small water content.

16. The method according to claim 11, wherein, in the process of preparing the compound of formula (VI), the molar ratio of alkyl acetate (II) to alkoxide (III) is from 0.8:1 to 10:1.

17. The method according to claim 11, wherein, in the process of preparing the compound of formula (VI), the molar ratio of alkyl difluoroacetate (IV) to alkyl acetate (II) is from 1:0.8 to 1:20.

18. The method according to claim 11, wherein, in the process of preparing the compound of formula (VI), the molar ratio of alkoxide (III) to acid is from 1:0.7 to 1:5.

19. The method according to claim 11, wherein, in the process of preparing the compound of formula (VI), the reaction temperature for the reaction of (II), (III) and (IV) is from −20° C. up to 70° C.

* * * * *

UNITED STATES PATENT AND TRADEMARK OFFICE
CERTIFICATE OF CORRECTION

PATENT NO. : 8,207,354 B2
APPLICATION NO. : 12/919842
DATED : June 26, 2012
INVENTOR(S) : Volker Maywald et al.

It is certified that error appears in the above-identified patent and that said Letters Patent is hereby corrected as shown below:

In Claim 10, col. 9, line 42, delete "alkosymethylene" and insert --alkoxymethylene--; and
col. 10, line 36, delete "difluoroacetate" and insert --difluoroacetoacetate--.

Signed and Sealed this
Second Day of October, 2012

David J. Kappos
*Director of the United States Patent and Trademark Office*